(12) United States Patent  
Blizzard et al.

(10) Patent No.: US 10,897,895 B2  
(45) Date of Patent: Jan. 26, 2021

(54) THERMOPLASTIC MATERIALS HAVING BENEFICIAL PROPERTIES AND PROCESSES FOR PROVIDING THE SAME

(71) Applicants: John D. Blizzard, Midland, MI (US); Joan McMahon, Midland, MI (US); Michael Silver, Lake City, MI (US)

(72) Inventors: John D. Blizzard, Midland, MI (US); Joan McMahon, Midland, MI (US); Michael Silver, Lake City, MI (US)

(73) Assignee: QuadSil, Inc., Midland, MI (US)

( * ) Notice: Subject to any disclaimer, the term of this patent is extended or adjusted under 35 U.S.C. 154(b) by 227 days.

(21) Appl. No.: 15/874,061

(22) Filed: Jan. 18, 2018

(65) Prior Publication Data

US 2018/0171109 A1 Jun. 21, 2018

Related U.S. Application Data

(60) Provisional application No. 62/435,351, filed on Dec. 16, 2016.

(51) Int. Cl.

| | |
|---|---|
| A01N 33/12 | (2006.01) |
| A01N 25/10 | (2006.01) |
| A01N 25/34 | (2006.01) |
| A46D 1/00 | (2006.01) |
| C08J 3/12 | (2006.01) |
| C08J 3/20 | (2006.01) |
| C08K 5/544 | (2006.01) |
| A01N 59/10 | (2006.01) |
| A61K 8/02 | (2006.01) |
| A61K 8/21 | (2006.01) |
| A61K 8/88 | (2006.01) |
| A61K 8/87 | (2006.01) |
| A61Q 11/00 | (2006.01) |
| A61K 8/58 | (2006.01) |

(Continued)

(52) U.S. Cl.
CPC .............. *A01N 33/12* (2013.01); *A01N 25/10* (2013.01); *A01N 25/34* (2013.01); *A01N 59/10* (2013.01); *A46B 9/04* (2013.01); *A61K 8/0216* (2013.01); *A61K 8/21* (2013.01); *A61K 8/585* (2013.01); *A61K 8/87* (2013.01); *A61K 8/88* (2013.01); *A61Q 11/00* (2013.01); *C02F 1/50* (2013.01); *C08G 69/48* (2013.01); *C08J 3/005* (2013.01); *C08J 3/128* (2013.01); *C08J 3/203* (2013.01); *C08K 5/544* (2013.01); *D01F 1/02* (2013.01); *D01F 1/103* (2013.01); *A46B 2200/1066* (2013.01); *A46D 1/006* (2013.01); *A61K 2800/87* (2013.01); *A61K 2800/92* (2013.01); *C02F 2303/04* (2013.01); *C08J 2375/04* (2013.01); *C08J 2375/06* (2013.01); *C08J 2377/02* (2013.01); *C08J 2477/02* (2013.01)

(58) Field of Classification Search
None
See application file for complete search history.

(56) References Cited

U.S. PATENT DOCUMENTS

2007/0048358 A1* 3/2007 Schorr .................... A01N 25/34  
424/443  
2015/0044449 A1* 2/2015 Foss ........................ A01N 25/10  
428/221

* cited by examiner

*Primary Examiner* — Bethany P Barham  
*Assistant Examiner* — Barbara S Frazier

(57) ABSTRACT

Methods of providing sustained sterilization of thermoplastics; providing thermoplastics that have the capacity to dispense sodium fluoride, and, a method of providing sustained sterilization of thermoplastics and providing thermo- (Continued)

plastics that have the capacity to dispense sodium fluoride, both from the same thermoplastic article.

25 Claims, 1 Drawing Sheet

(51) Int. Cl.
*C02F 1/50* (2006.01)
*A46B 9/04* (2006.01)
*D01F 1/02* (2006.01)
*C08J 3/00* (2006.01)
*C08G 69/48* (2006.01)
*D01F 1/10* (2006.01)

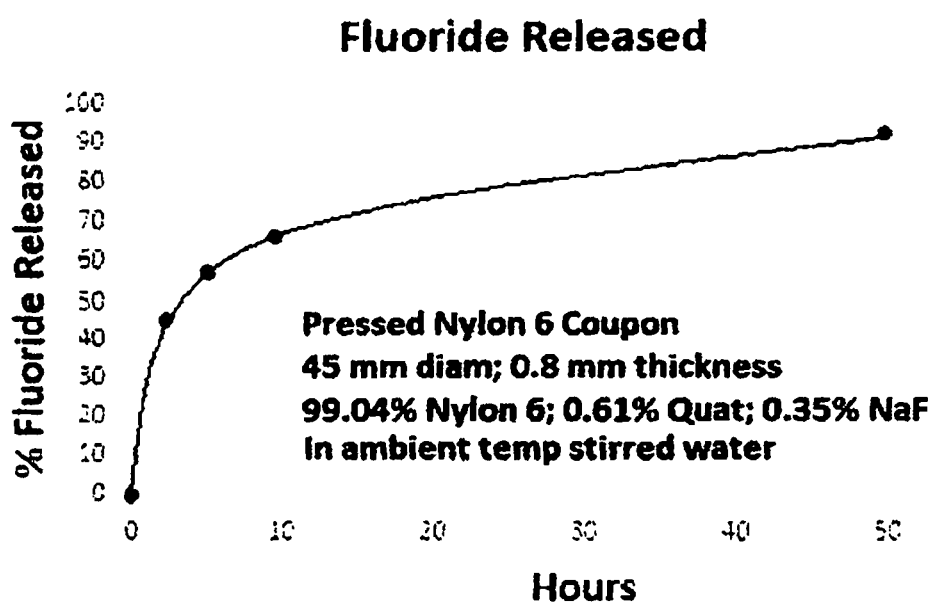

THERMOPLASTIC MATERIALS HAVING BENEFICIAL PROPERTIES AND PROCESSES FOR PROVIDING THE SAME

BACKGROUND OF THE INVENTION

Silanes possessing one or more hydrolysable groups that yield silanol (Si—OH) functionalities have been for the past five decades, and continue to be, useful for coating and functionalizing surfaces of many different substances. Most typically, the hydrolysable groups are methoxy (Si—OCH$_3$) and ethoxy (Si—OCH$_2$CH$_3$) which react with water to yield the aforementioned silanol groups.

The surfaces to be coated fall generally into three groups: Type I: Surfaces that possess accessible hydroxyl (OH) or oxide (O) groups, such as surfaces found in, but not limited to, many metals, metal oxides, silica, titanium, cotton, rayon, and cellulose. Type II: Surfaces that lack hydroxyl and oxide groups but that possess functionalities capable of hydrogen bonding such as but not limited to surfaces found in polyurethanes, polyamides, polyesters, and blends therein. In general, any of the silanol groups on a silane will bond covalently to Type 1 surfaces via the condensation reaction shown below:

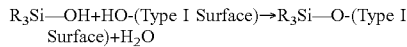

This yields a robust, "permanent" coating of silane on Type I surfaces as the attachment to the silane are via one or more covalent bonds depending on the number of silanol groups on the silane. This is in contrast to Type II surfaces, where the strongest interaction between silane Si—OH groups and the surface is due to hydrogen bonding, typically between the silanol hydrogen atom and a nitrogen atom, an oxygen atom, or a carboxyl oxygen atom present in the material (and unreactive towards condensation with a silanol) that is present in the Type II surface.

Since a hydrogen bonding interaction is weaker than a covalent bond, the silane coating on a Type II surface can be expected to be less robust and less permanent than for Type I surfaces. Finally, Type III surfaces are those made of materials such as, but not limited to, polyethylene, polypropylene or nylon that possess no functionalities capable of forming covalent bonds or hydrogen bonding interactions with a silanol functionality on a silane. For these surfaces, a silane coating would be secured by weaker van der Waal's forces and could be expected to be the least robust with respect to wear and leaching by a solvent.

Nevertheless, the use of silanol-functional silanes for surface coatings has not been limited to just Type I surfaces. For example, in 1981, the EPA granted Dow Corning the use of Dow Corning 5700, a methanol solution of 3-(trimethoxysilyl)propyldimethyloctadecyl ammonium chloride, on carpeting via pad, spray, or foam application for the purposes of rendering carpeting antimicrobial. Studies indicated that the resulting silane coating produced antimicrobial benefits for Nylon carpeting even after repeated washings and wear. Unfortunately, where such silane coatings fall short is on bristles that possess Type II and Type III surfaces commonly used to make cleaning brushes and toothbrushes.

Brush bristles of these types are made from thermoplastics such as Nylon whereby pellets or chips of the thermoplastic polymer are fed into a hopper, melted in a screw-type extruder, and extruded into bristle filaments through a spinneret in a process known as spin melting. Silane coatings perform poorly for such bristles because the weaker attachment of the silane coating to Type II and Type III surfaces renders the coating susceptible to wear when used in combination with abrasive cleaners (many cleaning and toothpaste formulations contain hard abrasive particles) and leaching (these brushes are often rinsed many, many times over their useful lifetime with warm or hot water).

A present method to render brush bristles possessing Type II and Type III surfaces permanently antimicrobial is to incorporate silver nanoparticles into their bulk and surface during the melt portion of the melt-spin bristle production process. Upon cooling, the silver nanoparticles become entrapped in the solidified thermoplastic. However, due to the high cost of silver nanoparticles and the fact that bristles incorporating them tarnish (grey) in relatively short order, they have not proved to be a satisfactory solution.

Another method that makes parts from thermoplastics that yield Type II and Type III surfaces is injection molding. As in melt-spinning, pellets or chips of the thermoplastic are melted and then injected under pressure into a mold, and silver nanoparticles can again be introduced into the melt pre-injection. Incorporation of antimicrobial silanes such as 3-(trimethoxysilyl)propyldimethyloctadecyl ammonium chloride via incorporation into the polymer melt during the spin melt or injection mold process has been unsuccessful due to thermal decomposition of the silane and scorching of the resulting polymer due to the high temperatures required for polymer melting. For example, 3-(trimethoxysilyl)propyldimethyloctadecyl ammonium chloride begins to thermally decompose at 125° C., whereas Nylon 6 requires temperatures ranging from 260-300° C. for melt-spinning and injection molding.

Thus, even though much less expensive than silver nanoparticles and non-tarnishing, antimicrobial silanes have not been successfully incorporated into thermoplastic fibers and parts via introduction and dispersing of the silane into the melt during melt-spinning and injection molding. What would be extremely beneficial is a method that allows for incorporation of silanes, and in particular, silanes with antimicrobial activity, into fibers and parts made from thermoplastics via introduction into the melted thermoplastic without any or with minimal amount of scorching or discoloring.

It is well-known that sodium fluoride has been used for protecting teeth from decay. Thus, in addition to treatments of teeth by dentists, sodium fluoride is incorporated into toothpaste as a means of delivering the sodium fluoride to teeth. It would be convenient and less awkward if a means of delivering sodium fluoride to teeth could be discovered.

The compositions of the instant invention are such a means of delivering sodium fluoride to teeth.

BRIEF DESCRIPTION OF THE DRAWINGS

FIG. 1 shows release of fluoride from nylon coupon.

THE INVENTION

Thus, what is described herein in one embodiment is a method of providing sustained sterilization of thermoplastics said method comprising providing a hydrolyzate of a silane having the general formula: $(RO)_3Si(CH_2)nN^+(R')_2(R'')Cl^-$ wherein R is an alkoxy group having 1 to 4 carbon atoms, n has a value of 3 to 8, each R' is selected from alkyl groups having 1 to 4 carbon atoms, and R" is the radical —$(CH_2)mCH_3Cl^-$ wherein m has a value of 12 to 20; coating particulates of said thermoplastic with said hydrolyzate; heating and drying said coated particulates to yield dry coated particulates; providing said coated particulates as feedstock for providing thermoplastic products by a process selected from the group consisting of: melt-spinning and injection molding.

Contemplated within the scope of this invention are compositions provided by this process and articles provided from the compositions of this process.

In a second embodiment, there is a method of providing thermoplastics that have the capacity to dispense sodium fluoride, said method comprising: adding a desired amount of sodium fluoride to water to form a solution; coating particulate thermoplastics with said solution thereafter heating and drying said particulate thermoplastics; providing said coated particulates as feedstock for a process selected from melt-spinning and injection molding.

Contemplated within the scope of this invention are compositions provided by this process and articles provided from the compositions of this process.

In yet a third embodiment there is a method of providing sustained sterilization of thermoplastics and providing thermoplastics that have the capacity to dispense sodium fluoride, both from the same thermoplastic, said method comprising providing a hydrolyzate of a silane having the general formula:

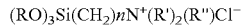

$(RO)_3Si(CH_2)nN^+(R')_2(R'')Cl^-$ wherein R is an alkoxy group having 1 to 4 carbon atoms, n has a value of 3 to 8, each R' is selected from alkyl groups having 1 to 4 carbon atoms, and R" is the radical —$(CH_2)mCH_3Cl^-$ wherein m has a value of 12 to 20; adding a desired amount of sodium fluoride solution to said hydrolyzate; coating particulates of said thermoplastic with said hydrolyzate containing said sodium fluoride; heating and drying said coated particulates to yield dry coated particulates; providing said coated particulates as feedstock for providing thermoplastic products by a process selected from the group consisting of melt-spinning and injection molding.

Contemplated within the scope of this invention are compositions provided by this process and articles provided from the compositions of this process.

DETAILED DESCRIPTION OF THE INVENTION

What has been discovered is a method that allows for solventless incorporation of silanes into thermoplastics during the melting of the thermoplastic without scorching of the thermoplastic part. Furthermore, this method also results in thermoplastic parts that demonstrate substantial antimicrobial activity for incorporation of silanes that are also proven to demonstrate antimicrobial activity.

An aqueous solution of a silane is prepared and allowed sufficient time with appropriate pH adjustment and dilution to achieve a solution or dispersion of completely hydrolyzed silane (hydrolyzate).

The silanes can be purchased from Dow Corning Corporation, Midland, Mich. and consist of silanes such as (RO)$_3$Si(CH$_2$)n-N$^+$(R')$_2$(R")Cl$^-$ wherein R is an alkoxy group having 1 to 4 carbon atoms, n has a value of 3 to 8, each R' is selected from alkyl groups having 1 to 4 carbon atoms, and R" is the radical —(CH$_2$)mCH$_3$Cl$^-$ wherein m has a value of 12 to 20. Preferred silanes are those having methoxy groups or ethoxy groups and an alkyl radical wherein m is 14 to 20, most preferred are methoxy groups and m equal to 18.

Such a molecule is $(CH_3 O)_3Si(CH_2)_3N^+(CH_3)_2(C_{18}H_{37})Cl^-$.

The hydrolyzate is then applied to a particulate thermoplastic such as pellets, or chips, and this can be accomplished in at least two ways. One method is to spray coat the particulates while agitating them in a container and the other way is to simply immerse the particulate thermoplastics into the hydrolyzate, both at room temperature.

The coated beads are then subjected to mild heat and drying to yield dry coated particulates. The dried coated particulates can then be used as is in a melt spinning operation or in injection molding. The heat and drying can be accomplished by forced hot air with the aid of an oven, a vacuum oven, a forced hot air dryer, or a coating machine capable of forced hot air drying, with drying occurring until further drying causes no significant loss of mass, insuring removal of the water.

It is believed that the unexpected success of this method (incorporation of the silane without scorching and survival of antimicrobial activity of the extruded or molded part despite the high temperatures involved in melting the thermoplastic) is due to the use of aqueous solutions of application of the silane to the particulate thermoplastics and the use of low heat when drying.

Additionally, we have discovered that soaking the final thermoplastic part in ambient water allows for a release of sodium fluoride into aqueous solution.

The compositions are useful for providing articles that are antimicrobial in nature. The compositions are also useful for delivering sodium fluoride, such as, for example, from toothbrush bristles while brushing teeth. It is also contemplated that the compositions would be useful for other brush configurations and as a woven mesh, for example in the application of clarifying and sterilizing water for drinking.

Examples of thermoset plastics that are useful in this invention include, for example, nylon, acrylic, polyurethanes, ethylene vinyl acetate. Especially useful are polyurethane polyesters and nylon.

Dental retainers are manufactured from acrylic resin thermoplastics, aligners used for movement of teeth are manufactured from polyurethane thermoplastics, boil-and-bite mouth guards are manufactured from ethylene vinyl acetate thermoplastics, mouth guards are injection molded from thermoplastics, and elastomeric orthodontic ligatures are manufactured from polyester polyurethanes.

Antimicrobial active Mouth guards used by children, especially children with braces, is a huge need as mouth guards get dirty pretty easily and children with braces more commonly have exposed cuts which presents a greater risk of infection.

EXAMPLES

The following examples illustrate the inventive method and are not meant to be limiting in any way to the general method outlined Supra, nor are the percentages of components indicated meant to be limiting, but are only illustrative.

The source of the silane was Dow Corning 5772, a 72% solution of 3-(trimethoxysilyl)propyldimethyl-octadecyl ammonium chloride in methanol. From this, a stable pH 9-10 3.6% solution of 3-(trihydoxysilyl) propyldimethyloctadecyl ammonium chloride (hydrolyzate) was prepared via 24 hour hydrolysis via aqueous dilution and addition of NaOH, with methanol removed via vacuum stripping. This was a clear pale orange solution upon formation (marketed by QuadSil Inc., Midland, Mich. as QS72-5), but became a stable milky dispersion upon standing for many weeks. Either form was successfully employed for proof of concept.

Addition of sodium fluoride from 0.8-2.0% by mass rapidly converted both the solution and the dispersion to a stable gel.

Example 1

QuadSil QS72-5 (124.15 g) was combined and stirred with 1.035 g NaF to yield a stable gel.

Example 2

BASF Ultramid 8202 Polyamide 6 (Nylon 6) (10.0 g of approx. 3 mm diameter pellets) were coated with a total of 4.488 g of gel from Example 1 in a Pyrex® beaker and then stirred and dried while heating on a hot plate (>300° C.) and with the aid of a hot air gun. The result was a dry whitish coating on the pellets. Note that such heating and drying could also be accomplished using an oven or a coating machine typically used to coat tablets and candies. The dried coating represented 1.79% of the total mass of the coated pellets (1.45% 3-(trihydroxysilyl)propyldimethyloctadecyl ammonium chloride (hydrolyzate); 0.34% NaF). Approximately 20 pellets were placed in an aluminum weigh boat and heated on a hot plate (cycling between 324-353° C.) to melting while being stirred with a stainless steel spatula, which was subsequently used to press a flat coupon. The coupon, upon cooling, demonstrated no visible scorching. Coupons were also prepared in a similar manner using uncoated pellets.

Example 3

Bayer Texin® 285 aromatic (20.4 g of approx. 3 mm diameter pellets) were coated with a total of 10.105 g of gel from Example 1 in a Pyrex beaker and then stirred and dried while heating on a hot plate (>300° C.) and with the aid of a hot air gun. The result was a dry whitish coating on the pellets. Note that such heating and drying could also be accomplished using an oven or a coating machine typically used to coat tablets and candies. The dried coating represented 1.23% of the total mass of the coated pellets (1.05% 3-(trihydroxysilyl) propyldimethyloctadecyl ammonium chloride (hydrolyzate); 0.18% NaF). Approximately 20 pellets were placed in an aluminum weigh boat and heated on a hot plate (cycling between 324-353° C.) to melting while being stirred with a stainless steel spatula, which was subsequently used to press a flat coupon. The coupon, upon cooling, demonstrated no visible scorching. Coupons were also prepared in a similar manner using uncoated pellets.

Example 4: Antimicrobial Activity Evaluation of Treated Nylon and Polyurethane Thermoplastics Antimicrobial activity employing *Staphylococcus aureus* was performed using Shake Test ASTM Method E2149-10 and samples Example 2 and 3. The results are presented in Table I.

| Material | Avg. CFU/ml | % Reduction |
|---|---|---|
| | Two Hour | |
| Bacteria Control | $3.32 \times 10^5$ | Not applicable |
| Untreated Ultramid 8202 Nylon 6 | $1.32 \times 10^5$ | 60 |
| Untreated Texin 286 Polyurethane | $1.76 \times 10^5$ | 47 |
| Example 2 coupon | $1.2 \times 10^4$ | 96 |

| Material | Avg. CFU/ml | % Reduction |
|---|---|---|
| Example 3 coupon | $1.32 \times 10^5$ | 60 |
| | Four Hour | |
| Bacteria Control | $3.08 \times 10^5$ | Not applicable |
| Untreated Ultramid 8202 Nylon 6 | $2.8 \times 10^5$ | 9 |
| Untreated Texin 286 Polyurethane | $2.64 \times 10^5$ | 14 |
| Example 2 coupon | $8.0 \times 10^3$ | 97 |
| Example 3 coupon | $2.4 \times 10^4$ | 92 |

Example 5

QuadSil QS72-5 (49.04 g) of was combined and stirred with 1.00 g NaF to yield a stable gel.

Example 6

BASF Ultramid® 8202 Polyamide 6 (Nylon 6) (20.30 g of approx. 3 mm diameter pellets) were coated with a total of 8.56 g of gel from Example 5 in a Pyrex beaker and then stirred and dried while heating on a hot plate (>300° C.) and with the aid of a hot air gun. The result was a dry whitish coating on the pellets. Note that such heating and drying could also be accomplished using an oven or a coating machine typically used to coat tablets and candies. The dried coating represented 1.65% of the total mass of the coated pellets.

Additional uncoated BASF Ultramid 8202 Polyamide pellets (14.78 g) were added to the coated pellets. This yielded a batch of pellets that were 99.04% Nylon, 0.61% 3-(trihydroxysilyl)propyldimethyloctadecyl ammonium chloride (hydrolyzate), and 0.35% NaF. Approximately 2 g of pellets were placed in a circular aluminum weigh boat (50 mm diameter) and heated on a hot plate (approx. 380° C.) to melting while pressing down on the pellets with the flat end of a Pyrex beaker (while rotating the beaker to simulate stirring of the melt) for 2.5 minutes, to yield a 0.8 mm thick flat coupon. The coupon, upon cooling, demonstrated no visible scorching. Coupons were also prepared in a similar manner using uncoated pellets.

Example 7

A 1.024 g circular coupon (0.8 mm thick, 43 mm diameter; 99.04% Nylon, 0.61% 3-(trihydroxysilyl)propyldimethyloctadecyl ammonium chloride (hydrolyzate), and 0.35% NaF) trimmed from an Example 6 coupon, was placed into a 300 mL beaker along with a magnetic stir bar and 200.0 g of RO water. The beaker was covered to prevent evaporation and the contents were stirred. Fluoride concentration was measured with a fluoride selective electrode as a function of time. The results are plotted in FIG. 1.

Example 8: Antimicrobial Activity Evaluation of Treated Nylon

Antimicrobial activity employing *Staphylococcus aureus* and *Escherichia coli* was performed using Test JIS Z 2801 "Antimicrobial Products—Test for antimicrobial activity and efficacy" and samples from Example 6. The bacteria were in direct contact with the test material and covered with a coverslip in a humidity chamber for specified time points, then neutralized, dilutions made and plated out. The results are presented in Tables II and III.

TABLE II (*Staphylococcus aureus*) - Sixty Minute Time Point

| Material | Average CFU/ml | % Reduction | Log Reduction |
|---|---|---|---|
| Control | $3.23 \times 10^4$ | Not applicable | Not applicable |
| Treated | $3.3 \times 10^1$ | 99.9 | 3 |

TABLE III (*Escherichia coli*) - Sixty Minute Time Point

| Material | Average CFU/ml | % Reduction | Log Reduction |
|---|---|---|---|
| Control | $2.56 \times 10^4$ | Not applicable | Not applicable |
| Treated | $5.67 \times 10^3$ | 77.9 | 0.6 |

What is claimed is:

1. A method of providing a thermoplastic material, said method comprising:
   A. providing a hydrolyzate of a silane having the general formula:

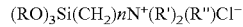
   $(RO)_3Si(CH_2)nN^+(R')_2(R'')Cl^-$ wherein R is an alkoxy group having 1 to 4 carbon atoms, n has a value of 3 to 8, each R' is selected from alkyl groups having 1 to 4 carbon atoms, and R" is the radical —$(CH_2)mCH_3Cl^-$ wherein m has a value of 12 to 20;
   B. coating particulates of a thermoplastic with said hydrolyzate;
   C. heating and drying said coated particulate thermoplastics to yield dry coated thermoplastic particulates;
   D. providing said coated thermoplastic particulates as feedstock for providing a thermoplastic material by a process selected from the group consisting of:
      i. melt-spinning, and
      ii. injection molding; wherein the thermoplastic material reduces the growth of bacteria or micro-organisms.

2. The method of claim 1, wherein said bacteria reduced are Gram-positive bacteria and/or Gram-negative bacteria.

3. The method of claim 1, wherein said feedstock for providing thermoplastic material further comprises an amount of uncoated thermoplastic particulates.

4. The method of claim 1, wherein said coated particulate thermoplastic material is mixed with an additional thermoplastic material that is not the same as said coated particulate thermoplastic material.

5. The method of claim 1, wherein said coating is provided by spraying said hydrolyzate onto said particulate thermoplastic while agitating said particulate thermoplastic.

6. The method of claim 1, wherein said coating is provided by adding said hydrolyzate to said particulate thermoplastic while agitating said particulates.

7. A method of providing a thermoplastic material, said method comprising:
   A. providing a hydrolyzate of a silane having the general formula:

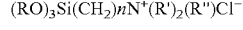
   $(RO)_3Si(CH_2)nN^+(R')_2(R'')Cl^-$ wherein R is an alkoxy group having 1 to 4 carbon atoms, n has a value of 3 to 8, each R' is selected from alkyl groups having 1 to 4 carbon atoms, and R" is the radical —$(CH_2)mCH_3Cl^-$ wherein m has a value of 12 to 20;
   B. adding a desired amount of sodium fluoride solution to said hydrolyzate;
   C. coating particulates of a thermoplastic with said hydrolyzate containing said sodium fluoride;
   D. heating and drying said coated particulates to yield dry coated thermoplastic particulates;
   E. providing said coated thermoplastic particulates as feedstock for providing a thermoplastic material by a process selected from the group consisting of:
      i. melt-spinning, and
      ii. injection molding; wherein the thermoplastic material reduces the growth of bacteria or micro-organisms; and wherein the thermoplastic material has the capacity to dispense the sodium fluoride.

8. The method of claim 7, wherein said bacteria reduced are Gram-positive bacteria and/or Gram-negative bacteria.

9. The method of claim 7, wherein said feedstock for providing thermoplastic material further comprises an amount of uncoated thermoplastic particulates.

10. The method of claim 7, wherein said coated particulate thermoplastic is mixed with an additional thermoplastic material that is not the same as said coated particulate thermoplastic material.

11. The method of claim 7, wherein said coating is provided by spraying said solution onto said particulate thermoplastic while agitating said particulate thermoplastic.

12. The method of claim 7, wherein said coating is provided by adding said solution to said particulate thermoplastic while agitating said particulate thermoplastic.

13. The method of claim 1, wherein said thermoplastic particulate is nylon.

14. The method as claimed in claim 7, wherein said thermoplastic particulate is nylon.

15. The method of claim 1, wherein said thermoplastic is selected from the groups consisting of:
   i. nylon,
   ii. acrylic,
   iii. polyurethanes, and
   iv. ethylene vinyl acetate.

16. The method of claim 15, wherein said thermoplastic is polyurethane polyester.

17. The method of claim 1, wherein said thermoplastic material is selected from the group consisting of:
   i. dental retainers,
   ii. teeth aligners,
   iii. boil-and-bite mouth guards,
   iv. mouth guards, and
   v. elastomeric orthodontic ligatures.

18. The method of claim 1, wherein said bacteria reduced is a coccus bacterium; and/or
   wherein said bacteria reduced is a bacilliform bacterium.

19. The method of claim 1, wherein said bacteria reduced is an *Escherichia* bacterium; and/or
   wherein said bacteria reduced is a *Staphylococcus* bacterium.

20. The method of claim 1, wherein said bacteria reduced is a facultatively anaerobic bacteria.

21. The method of claim 1, wherein said bacteria reduced is *Staphylococcus aureus*; and/or
   wherein said bacteria reduced is *Escherichia coli*.

22. The method of claim 7, wherein said bacteria reduced is a coccus bacterium; and/or
   wherein said bacteria reduced is a bacilliform bacterium.

23. The method of claim 7, wherein said bacteria reduced is an *Escherichia* bacterium; and/or
wherein said bacteria reduced is a *Staphylococcus* bacterium.

24. The method of claim 7, wherein said bacteria reduced is a facultatively anaerobic bacteria.

25. The method of claim 7, wherein said bacteria reduced is *Staphylococcus aureus*; and/or
wherein said bacteria reduced is *Escherichia coli*.

* * * * *